United States Patent [19]
Armini et al.

[11] Patent Number: 6,010,445
[45] Date of Patent: Jan. 4, 2000

[54] RADIOACTIVE MEDICAL DEVICE AND PROCESS

[75] Inventors: Anthony J. Armini, Manchester; Stephen N. Bunker, Wakefield, both of Mass.

[73] Assignee: Implant Sciences Corporation, Wakefield, Mass.

[21] Appl. No.: 08/968,982

[22] Filed: Nov. 12, 1997

Related U.S. Application Data

[60] Provisional application No. 60/058,490, Sep. 11, 1997, and provisional application No. 60/059,370, Sep. 19, 1997.

[51] Int. Cl.$^7$ ...................................................... A61N 5/00
[52] U.S. Cl. ............................. 600/3; 600/1-8; 606/191; 606/198; 623/1; 623/12
[58] Field of Search ............................ 600/1–8; 606/191, 606/198; 623/1, 12

[56] References Cited

U.S. PATENT DOCUMENTS

| 4,469,483 | 9/1984 | Becker et al. | 604/280 |
|---|---|---|---|
| 4,584,991 | 4/1986 | Tokita et al. | 128/1.1 |
| 4,586,490 | 5/1986 | Katz | 128/1.1 |

(List continued on next page.)

OTHER PUBLICATIONS

Hessel et al, "Angiography and Vasa Vasorum Blood Flow after Aortic Dilation," *Investigative Radiology* (Sep.–Oct.) p. 404 (1978).

Goldberg et al, "In Vivo Aortic Smooth Muscle Cell (SMC) Kinetics: Responnse to Irradiation in the Rat," *Cell Tissue Kinet,* vol. 15, No. 6, p. 675 (1982).

Lee et al, "Effects of Laser Irradiation on Cardiac Valves Technique of Trans Catheter in Vivo Vaporization of Aortic Valve," *Laser Surg. Med.* vol. 3, No. 2, pp. 174–175 (1983).

Lee et al, "Laser Irradiation of Human Atherosclerotic Obstructive Disease: Simultaneous Visualization and Vaporization Achieved by a Dual Fiberoptic Catheter," *American Heart Journal,* vol. 105, No. 1, pp. 163–164 (1983).

Lee et al, "Effects of Laser Irradiation on Cardiac Valves Trans Catheter in Vivo Vaporization of Aortic Valve," *American Heart Journal,* vol. 107, p. 394 (Feb. 1984).

Solomon et al, "An In Vivo Method for the Evaluation of Catheter Thrombogenicity," *Journal of Biomedical Materials Research,* vol. 21, pp. 43–57 (1987).

Rosch et al, "Gianturco Expandable Wire Strents in the Treatment of superior Vena Cava Syndrome Recurring after Maximum Tolerance Radiation," *Cancer* (Phila), vol. 60, No. 6, pp. 1243–1246 (1987).

Daniel et al, "A New Rapid Safe Method for Local Radiation of Intrathoracic Sites," *Am. Surg.,* vol. 55, No. 9, pp. 560–562 (1989).

Tim A. Fischell, MD, et al., "Low–Dose, β–Particle Emission From 'Stent' Wire Results in Complete, Localized Inhibition of Smooth Muscle Cell Proliferation" in *Circulation* 90 pp. 2956–2963 (1994).

(List continued on next page.)

*Primary Examiner*—John P. Lacyk
*Attorney, Agent, or Firm*—Foley Hoag & Eliot LLP

[57] ABSTRACT

An implantable medical device according to the systems and methods described herein may include a metal body or stent that does not contain significant quantities of iron or chromium and that is initially formed from a non-radioactive structural material. A non-radioactive activatable additive (the precursor isotope) may be added into or onto the body of the medical device. Neutron activation of the body of the medical device with the incorporated non-radioactive isotope may then be accomplished, and, if the metal body of the medical device contains a significant quantity of nickel, a coating of a high-density material may be applied over the radioactive body of the medical device. In an alternate embodiment, a coating of certain types of high-density material may be applied prior to neutron activation. The coating of high-density material may serve several useful purposes, including containment of undesirable beta particles from spurious long-lived radioactive species, creation of a biologically inert surface, and enhancement of the x-ray radiopacity to improve the visibility of the implantable medical device.

15 Claims, 2 Drawing Sheets

U.S. PATENT DOCUMENTS

| | | | |
|---|---|---|---|
| 4,660,547 | 4/1987 | Kremer, Jr. | 128/1.1 |
| 4,714,074 | 12/1987 | Rey et al. | 128/1.1 |
| 4,715,359 | 12/1987 | Ryo | 128/1.1 |
| 4,733,665 | 3/1988 | Palmaz | 128/343 |
| 4,739,762 | 4/1988 | Palmaz | 128/343 |
| 4,776,337 | 10/1988 | Palmaz | 128/343 |
| 4,793,348 | 12/1988 | Palmaz | 128/325 |
| 4,803,977 | 2/1989 | Kremer, Jr. | 600/3 |
| 4,815,446 | 3/1989 | McIntosh | 600/3 |
| 4,881,937 | 11/1989 | van't Hooft et al. | 600/3 |
| 4,881,938 | 11/1989 | van't Hooft | 600/3 |
| 4,946,435 | 8/1990 | Suthanthiran et al. | 600/3 |
| 4,969,863 | 11/1990 | van't Hooft | 600/3 |
| 5,030,194 | 7/1991 | van't Hooft | 600/3 |
| 5,034,005 | 7/1991 | Appling | 604/280 |
| 5,059,166 | 10/1991 | Fischell et al. | 600/3 |
| 5,176,617 | 1/1993 | Fischell et al. | 600/3 |
| 5,256,158 | 10/1993 | Tolkoff et al. | 604/280 |
| 5,360,443 | 11/1994 | Barone et al. | 623/1 |
| 5,382,261 | 1/1995 | Palmaz | 606/158 |
| 5,395,300 | 3/1995 | Liprie | 600/3 |
| 5,498,250 | 3/1996 | Prather | 604/280 |
| 5,522,880 | 6/1996 | Barone et al. | 623/1 |
| 5,606,981 | 3/1997 | Tartacower et al. | 128/772 |
| 5,607,442 | 3/1997 | Fischell et al. | 606/191 |
| 5,632,771 | 5/1997 | Boatman et al. | 623/1 |
| 5,656,036 | 8/1997 | Palmaz | 623/12 |

OTHER PUBLICATIONS

Joseph G. Wiedermann, MD, et al., "Intracoronary Irradiation Markedly Reduces Restenosis After Balloon Angioplasty in a Porcine Model" in JACC, vol. 23, No. 6, pp. 1491–1498, May 1994.

Paul S. Teirstein, MD, et al., "Catheter–Based Radiotherapy to Inhibit Restenosis After Coronary Stenting" in *The New England Journal of Medicine,* vol. 336, No. 24 pp. 1697–1703 (1997).

John R. Laird, MD, et al., "Inhibition of Neointimal Proliferation With Low–Dose Irridation From a β–Particle–Emitting Stent" in Basic Science, pp. 529–536 (1995).

Vitali Verin, MD, et al., "Feasibility of Intracoronary β–Irradiation to Reduce Restenosis After Balloon Angioplasty" in Circulation, vol. 95, No. 5 pp. 1138–1143 (1997).

RADIOACTIVE MEDICAL DEVICE AND PROCESS

CROSS-REFERENCE TO RELATED APPLICATIONS

This application is based on and claims priority to U.S. provisional patent application serial No. 60/058,490, entitled "METHOD OF FABRICATING A RADIOACTIVE STENT", filed Sep. 11, 1997 and U.S. provisional patent application serial No. 60/059,370, entitled "RADIOACTIVE MEDICAL DEVICE AND PROCESS", filed Sep. 19, 1997, both of which are pending and are incorporated herein by reference.

BACKGROUND

After balloon angioplasty, a metal tubular scaffold structure called a stent may be permanently implanted to physically hold open the repaired coronary artery. Unfortunately, up to 30% of such procedures result in reclosure (restenosis) of the artery within six months to one year. One solution to the problem is to provide acute local, postoperative radiation treatment of the site using a catheter tipped with iridium-192 radioisotope. In this method the iridium-192 tipped catheter is placed at the arterial site for thirty to forty minutes after stent deployment and then retracted. This type of acute high dose treatment using gamma radiation has been found to substantially reduce the rate of subsequent restenosis, as noted in Wiedermann, J. G. et al., "Intracoronary Irradiation Markedly Reduces Restenosis After Balloon Angioplasty in a Porcine Model," 23 J. Am. Coll. Cardiol., 1491–1498 (May 1994) and Teirstein, P. S. et al., "Catheter-Based Radiotherapy to Inhibit Restenosis After Coronary Stenting," 336 New England Journal of Medicine, 1697–1703 (Jun. 12, 1997).

An alternate method of addressing the restenosis problem is to embed within the structural material of the stent itself a radioactive material as described by Fischell R. et al. in U.S. Pat. No. 5,059,166 (the '166 patent) and in U.S. Pat. No. 5,376,617 (the '617 patent). The '166 and '617 patents also describe a method of electroplating a radioactive material on the structural material of the stent. Each of these methods has certain drawbacks. Placement of radioactive material within the structural material of the stent can present fabrication difficulties with respect to radiation exposure of workers during the manufacturing process. The electroplating process may result in poor adhesion of the radioactive material, which could delaminate during insertion. Because of the typically short half lives of the isotopes commonly used for medical treatments, both methods suffer from the difficulty of having to continuously maintain a stock of rapidly decaying active isotopes in order that the activity may be embedded as soon as possible before the medical procedure is performed. The radioactive stent thus fabricated has relatively short "shelf life".

Moreover, an additional requirement for any clinically useful stent is that it should have good x-ray visibility. A fairly thick (ten to fifteen micrometer) radiopaque coating of a high-density, high atomic number metal such as gold, platinum, iridium, or rhenium may be coated on the structural material of the stent in order to achieve visibility in an x-ray. The '166 and the '617 patents mention the possibility of plating the radioisotope $Au^{198}$ on the structural material of the stent. Plating $Au^{198}$ would not make the stent radiopaque because the coating would be less than a few Angstroms thick. As noted by Fishell et al. in the article "Low-Dose β-Particle Emission From 'Stent' Wire Results in Complete, Localized Inhibition of Smooth Muscle Cell Proliferation", 90 Circulation 2956–2963 (1994) (the Fischell article), radioactivity on the order of one microcurie is preferred for a coronary stent. Using an $Au^{198}$ plating solution containing typically 18 Ci/g of dissolved gold (following a two-week cooldown period after activation in a nuclear reactor), a total activity of 1 $\mu$Ci would require a total coating mass of 0.055 $\mu$g, which, when distributed over the surface of an entire coronary stent, would have a thickness of about one atomic monolayer of gold. Such a thin layer would not add contrast in an x-ray picture of the stent. Moreover, $Au^{198}$ is not a pure beta ray emitter. It also emits numerous gamma rays, which may provide an undesirable radioactive dose to the entire body of a patient instead of a localized dose to a target area in the coronary artery.

Another method mentioned in the Fischell article and further investigated by Laird, J. R. et al., in "Inhibition of Neointimal Proliferation with Low-Dose Irradiation from a β-Particle-Emitting Stent," 93 Circulation 529 (Feb. 1, 1996) (the Laird article), is to impregnate titanium stents with up to thirty atomic percent of stable phosphorous and subsequently activate the entire stent in a nuclear reactor to form the radioisotope $P^{31}$ within the titanium structural material. One of the disadvantages of the Laird method is that the massive quantity (30 atomic percent) of phosphorous required to make even 0.15 microcurie of $P^{31}$ may severely alter the structural strength of the stent itself.

In the preferred embodiment of the '166 and '617 patents, the structural material in the body of the stent is alloyed with an activatable element and then subsequently activated in a nuclear reactor. When the body of a stent or any similar implantable medical device (including, without limitation, cancer irradiation needles, shunts, vascular grafts, bone screws, and femoral stem implants) contains significant quantities of iron and chromium, which is the case in stainless steel, for example, neutron activation produces long lived radioisotopes emitting a substantial quantity of gamma rays which generally would not be desirable for a permanent implant because of the high total body dose of radiation.

When the body of the medical device is fabricated from an alloy which includes the element nickel, the reactor activation produces significant quantities of the isotope nickel-63, which has a 100 year half life that is longer than the remaining lifetime of the human patient. Nickel is employed in shape-memory materials, such as NiTi, which is commonly known as nitinol. In nitinol, nickel is present with 50 atomic percent abundance. The radioactive decay of Ni-63 produces an undesirable background of low energy beta particles with an end point energy of 66.9 keV. While these beta particles have a relatively short range in tissue, approximately 0.08 mm, and may be partially absorbed within the nitinol, they are produced at a nearly constant rate for decades, and the total accumulated dose may, as a result, be undesirably high.

SUMMARY OF THE INVENTION

Coatings may be added to the surface of a medical device for specific purposes, such as for x-ray radiopacity, for blocking undesirable beta emissions from co-activated isotopes such as nickel-63, or for providing a more biologically inert surface than may be obtained with material, such as nitinol, that contains nickel. One of the objects of the systems and methods described herein is to provide intra-arterial medical implants used to restore patency to coronary arteries and, more specifically, to provide ferrous- and chromium-free radioactive medical implants with improved x-ray visibility.

A medical device according to the systems and methods described herein may include: a body being substantially free of iron and chromium; a high-density coating applied to at least a portion of the body; and a non-radioactive precursor isotope disposed about, associated with, or carried with the body and being capable of being transmuted in a nuclear reactor into a radioactive isotope having a half-life greater than approximately 16 hours and less than approximately 4 days.

A medical device according to the systems and methods described herein may also include: a body being substantially free of iron and chromium; a high-density coating applied to at least a portion of the body; and a radioactive isotope disposed about, associated with, or carried with the body, the radioactive isotope having a half-life greater than approximately 16 hours and less than approximately 4 days and having been transmuted in a nuclear reactor from a non-radioactive precursor isotope disposed about, associated with, or carried with the body.

The body may be formed from a material that includes a material selected from the group consisting of metals and metal alloys, including nitinol, rhenium or a rhenium alloy; from an organic polymer; or from a ceramic oxide. The non-radioactive precursor isotope may include at least one isotope selected from the group consisting of rhenium-185, rhenium-187, and tungsten-186. The non-radioactive precursor isotope addition may be disposed inside the body or may be disposed outside the body.

The high-density coating may include at least one element that thermal neutron activates substantially to radioisotopes with half-lives of less than approximately one day. The high-density coating may include at least one element selected from the group consisting of: titanium, vanadium, manganese, copper, praseodymium, and rhodium. The high-density coating may have a thickness that is greater than the range of 70 keV beta particles. The high-density coating may be between approximately five micrometers thick and approximately twenty micrometers thick.

An adhesion coating may be disposed between the body and the high density coating. The adhesion coating may include at least one element that thermal neutron activates substantially to radioisotopes with half-lives of less than approximately one day. The adhesion coating may include at least one material selected from the group consisting of: aluminum, silicon, titanium, vanadium, manganese, copper, nickel and rhodium.

A method of making a medical device according to the systems and methods described herein may include disposing a stable precursor element about a body that is substantially free of iron or chromium, applying a high-density coating to the body, and exposing the body, the high-density coating, and the stable precursor element to a source of thermal neutrons. The stable precursor element may be disposed inside the body or outside of the body. The stable precursor element may be added to the molten metal alloy of the medical device body, ion implanted into the body, coated onto the surface of the body, sputtered onto the surface of the body, applied by physical vapor deposition, electroplated onto the surface of the body, or some combination thereof. The high-density coating may be applied to at least a portion of the body by sputtering, physical vapor deposition, electroplating, or some combination thereof.

DETAILED DESCRIPTION OF THE PREFERRED EMBODIMENTS

Figure 1:
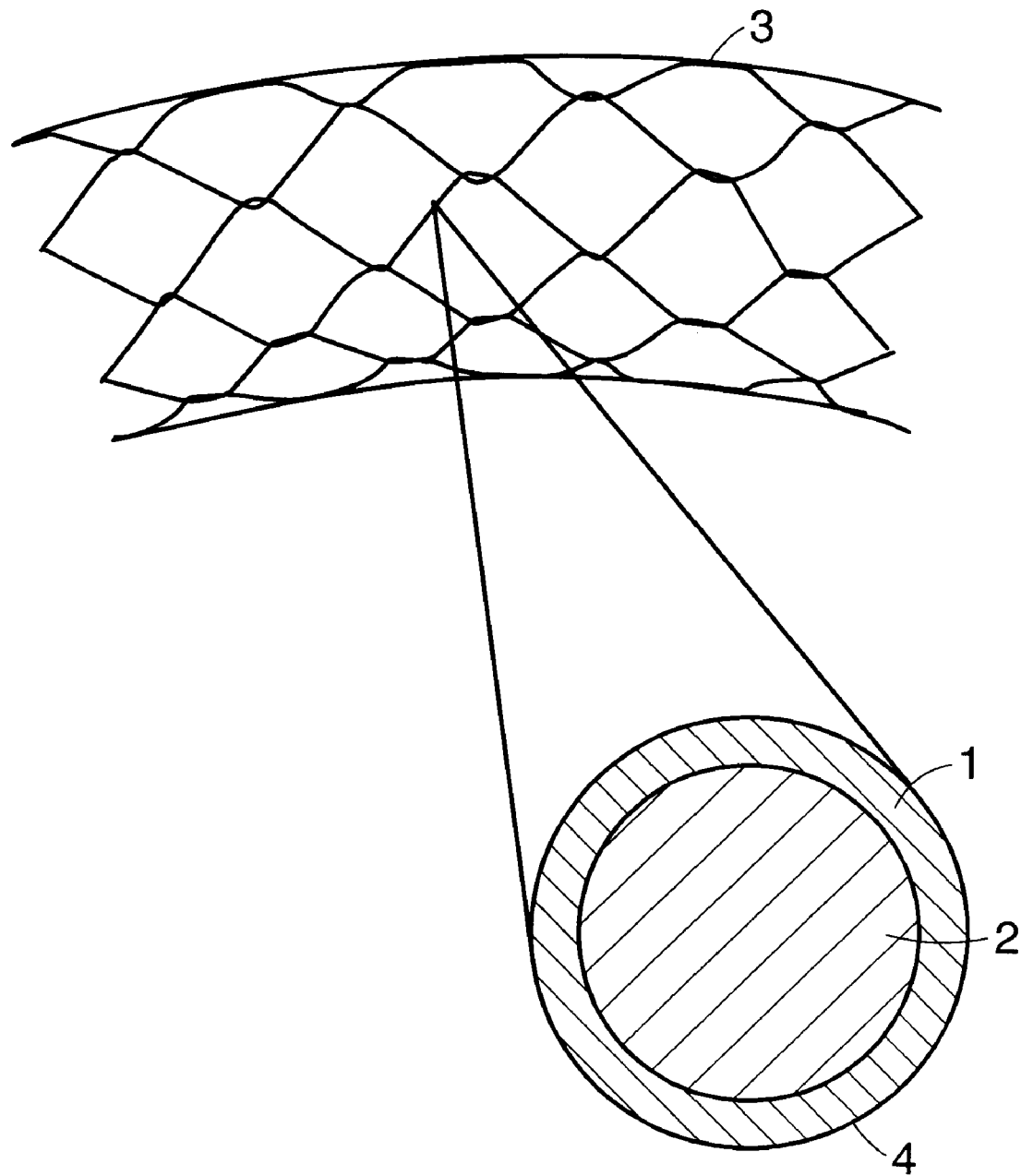
FIG. 1 illustrates a side-view and a cross-section of a single wire of a tubular mesh stent according to the present invention.

Many medical devices, including stents, are typically made from metals such as titanium alloy, nitinol (NiTi), or stainless steel. FIG. 1 shows an example of such a device used for opening coronary arteries called a stent. Medical devices made from alloys which do not contain substantial quantities of iron or chromium may also incorporate precursor isotopes that may be made therapeutically radioactive by immersion in a nuclear reactor. Coatings that enhance the safety and performance of these medical devices may be added either before or after the immersion in the nuclear reactor.

These devices may also be fabricated with included radioactive isotopes in order to inhibit restenosis. When the radioactive isotopes are produced by the neutron activation of the entire medical device in a nuclear reactor, the bulk material of the medical device may also be activated. If the medical device body contains significant quantities of nickel, undesirable long-lived emissions of nickel-63 typically are produced. A sufficient thickness of a high-density material may be used to block the passage of beta particles from nickel-63 into the surrounding tissue if the exposed surface of the medical device body is essentially completely covered with the high-density material.

Medical device bodies are commonly fabricated from alloys of stainless steel, such as type 404, and titanium-vanadium-aluminum alloy. Medical device bodies are also commonly fabricated from the intermetallic compound nickel-titanium (NiTi), known as nitinol. Neutron activation of NiTi produces a significant quantity of the spurious isotope nickel-63. This isotope decays solely by beta decay with no gamma radiation. The beta end-point energy is 66.9 keV. If a high-density coating is applied continuously over all of the exposed surfaces of the body of the medical device, the thickness can be selected to be in excess of the range of this beta particle. Without the blocking of the nickel-63 beta particles by the high-density coating, the nickel-63 beta particles would continuously bombard the artery wall around the stent body for the life of the patient, because the half life of nickel-63 is 100 years. Therapeutic medical isotopes are usually selected for their short half lives in order to limit the desired radiation dosage, and unshielded nickel-63 emissions are not desirable.

Nickel also is sometimes considered to be a source of undesirable metal ions in the human body. In nitinol the nickel is stabilized in the form of a compound. However, it still may be desirable to provide a coating of a protective, biologically inert material to eliminate any risk of nickel disolution into the bloodstream or other bodily fluids.

An implantable medical device according to the systems and methods described herein may include a metal body, or stent, that does not contain significant quantities of iron or chromium and that is initially formed from a non-radioactive structural material. A non-radioactive activatable additive (the precursor isotope) may be added into the body or onto the body of the medical device, i.e., by associating the isotope with the body or by disposing the isotope about the body. Neutron activation of the body of the medical device with the incorporated non-radioactive isotope may then be accomplished, and, if the metal body of the medical device contains a significant quantity of nickel, a coating of a high-density material may be applied over the radioactive body of the medical device. In an alternate embodiment, a coating of certain types of high-density material may be applied prior to neutron activation.

The coating of high-density material may serve several useful purposes, including containment of undesirable beta particles from spurious long-lived radioactive species, creation of a biologically inert surface, and enhancement of x-ray radiopacity to improve the visibility of the implantable medical device. The high-density coating preferably should have a thickness that is greater than the range of 70 keV beta particles, which is typically about 8.4 micrometers for gold and about 10 micrometers for rhodium.

The metal body of the medical device, which may be a titanium alloy, may have a tubular mesh shape, a helical coil shape, or a variety of other shapes. The composition of the body of the medical device may typically have a substantial fraction in the form of titanium, such as, for example, fifty atomic percent. Other alloying elements commonly employed may be vanadium, aluminum, or nickel. Optionally, one or more adhesion layers may be coupled to the body of the medical device to promote adhesion of the non-radioactive isotope precursor and/or the high-density coating material. The adhesion layer may be formed of a material that includes silicon, aluminum, titanium, vanadium, nickel, praseodymium, or rhodium when used between the non-radioactive stent body of the medical device and the non-radioactive isotope. When deposited onto a previously radioactivated body of the medical device, the adhesion layer may be formed of a material that includes silicon, titanium, vanadium, chromium, iron, cobalt, or nickel when used between the radioactive body of the medical device and the high-density coating material. When deposited onto a body of a medical device prior to neutron activation, the adhesion layer may be formed of a material that includes silicon, titanium, vanadium, manganese, or nickel. Materials containing substantial amounts of iron and chromium preferably should not be deposited as part of the adhesion layer or the high-density layer prior to neutron activation because such materials produce undesirable long-lived radioisotopes that emit gamma rays.

The selection of high-density coating materials and adhesion layer materials is dependent on whether these materials will be neutron activated. Only a limited group of elements will neutron activate solely to radioisotopes that are either stable, emit no radiation, or possess short radioactive decay half-lives of less than two days. Since the desirable therapeutic isotope generally has a half-life of between two days and thirty days, radioisotopes with shorter half-lives can be expected to decay to insignificant activity levels after a nominal decay time of fourteen days. For example, the element rhenium activates to Re-186 (3.777 day half-life) and Re-188 (0.708 day half-life). After fourteen days of decay and assuming equal quantities of initial activity, the activity ratio Re-188:Re-186 becomes $1.46 \times 10^{-5}:1$, which means that the amount of the short-lived isotope is insignificant. The elements aluminum, silicon, titanium, vanadium, manganese, copper, praseodymium, and rhodium meet the criterion of short half-life.

A non-radioactive isotope addition to the body of the medical device may include some percentage of other isotopes, such as, for example, rhenium-187, in addition to the precursor isotope, such as rhenium-185, that is specifically desired. The non-radioactive isotope addition may be optionally added to the body of the medical device by either incorporating a small quantity of the isotope into the molten alloy precursor from which the body of the medical device is fabricated, thermally diffusing the isotope into the body of the medical device, ion implanting with isotope mass separation below the surface of the body of the medical device, or coating the surface of the body of the medical device. Other methods for adding the non-radioactive isotope to the body of the medical device, such as electroplating or sputtering, may also be employed, either alone or in combination.

The criteria for selection of the stable element that is to be neutron activated include: having a half-life between two and thirty days; having a high neutron activation cross section; and having the resultant radioisotope primarily emit beta particles rather than gamma rays. The beta particles provide a short range dose to tissue, and thus the entire body of the patient does not receive a radiation dose unnecessarily. Radioisotopes that meet these criteria, to a greater or lesser extent, include, among others, phosphorous-32, phosphorous-33, sulfur-32, and rhenium-186. Phosphorous-32 has a low neutron activation cross section, phosphorous-33 is difficult to produce, sulfur-32 has too long a half-life, and rhenium-186 produces 20% of its radiation as gamma rays. When activating the entire medical device in a nuclear reactor, the preferred isotope is rhenium-186 made from the precursor rhenium-185. Elemental rhenium contains the precursor Re-185 as well as unused Re-187.

The quantity of desired non-radioactive isotope to be added to the implantable medical device body varies with the size of the body of the medical device. For example, a typical stent requires about ten to fifty micrograms of rhenium-185 or nearly five milligrams of phosphorous-31, with the difference primarily being related to the activation cross section and half-life. It is preferred that as much of the desired non-radioactive isotope be added as possible while avoiding a significant alteration in the desired physical and chemical properties of the medical device body. Larger concentrations of the non-radioactive precursor isotope are useful for minimizing neutron activation time and minimizing the incidental activation of spurious contaminating species in the medical device body. Isotopically enriched additions of the non-radioactive precursor isotope, such as enriched rhenium, which has approximately 98% rhenium-185 and approximately 2% rhenium-187 as opposed to the normal ratio of about three-eighths to five-eighths, may be optionally employed to advantage and would be preferred.

The medical device body is preferably fabricated from a material which does not contain substantial amounts of iron or chromium. The body may be fabricated from several types of materials commonly employed for medical devices. Typical metal alloys include Ti-6-4, which is 90% titanium, 6% vanadium, and 4% aluminum, and nitinol, which is 55% nickel and 45% titanium. Other possible materials include organic polymers and ceramic oxides, such as quartz (silicon dioxide), alumina (aluminum oxide), titania (titanium dioxide), and zirconia (zirconium oxide).

A special choice for a metal material for the medical device body would be rhenium, either in the form of a pure element or alloyed with another metal, such as vanadium, that meets the requirement of neutron activation to short half-lives, or nickel, which produces only low energy beta particles. While no medical devices are presently fabricated from rhenium or its alloys, this would be the preferred embodiment assuming that the mechanical and chemical requirements for the device could also be obtained. A medical device body fabricated from rhenium or its alloys would preferably be coated with a biologically inert substance, such as titanium, that also had the property of producing only short half-lives when exposed to thermal neutrons. The advantage of a medical device body containing a substantial quantity of rhenium would be that only a very short exposure to thermal neutrons would be required to achieve the desired therapeutic activity. The activation of impurities in the body would then be correspondingly diminished.

When the medical device body is thermal neutron activated, both the precursor isotope and any activatable impurity isotopes in the body may become radioactive. If the quantity of precursor isotope is increased, the required radioactivity level of the byproduct resulting from the precursor isotope then can be obtained with decreased neutron activation time. This in turn results in lower radioactivity levels due to the impurities in the medical device body. The quantity of non-radioactive precursor isotope is most easily increased by combining several of the methods described for precursor addition. For example, if elemental rhenium metal is sputtered onto the body as a coating while simultaneously ion implanting rhenium-185 atoms to improve adhesion, the rhenium metal can become a component of the high-density coating. Rhenium has a density of 21 grams/cm$^3$ and is an excellent radiopaque material. It is also more efficient then gold for absorbing nickel-63 beta particles, which have a range of 7.6 micrometers. In the preferred embodiment for coatings, another high-density coating material, such as rhodium or titanium, would be sputtered either simultaneously or during a portion of the deposition, such that the external surface of the high-density coating would consist solely of a biologically inert element. It is further preferred to gradually grade the concentration between pure rhenium and pure biologically inert element in order to enhance adhesion.

The technique of coating rhenium can yield as much as 1.5–2.0 milligrams of rhenium-185 added to a 17 milligram stent, depending on the surface area available for coating. This method of rhenium coating is primarily limited by adhesion and alteration of the mechanical properties of the stent. In contrast, the method of adding rhenium as an impurity to a molten stent alloy, such as nitinol, during manufacture is likely to be limited to only a few weight percent of rhenium, or about 0.075–0.15 milligrams of rhenium-185, in order to avoid modification of mechanical properties. If rhenium is added by ion implanting rhenium-185 while coating a high-density material such as rhodium, it is possible to add about 0.075 to 0.15 milligrams, depending on coating rate. If rhenium-185 is added by simply ion implanting the medical device body, only about 0.0015 milligrams can be obtained.

Ion implantation of a heavy element, such as rhenium, is normally limited because an equilibrium occurs between the addition of ions and their simultaneous loss due to sputtering, and this results in a comparatively low mass addition when ion implanting a medical device body. However, if ion implanting while simultaneously depositing a coating, the sputter loss then consists of atoms from the growing coating rather than those being ion implanted, yielding nearly 100% retention of implanted rhenium-185 atoms, which is about 100 times better than simple ion implantation. In comparison, if the entire stent were fabricated from rhenium, approximately 20 milligrams of rhenium-185 would be available for thermal neutron activation, an increase of a factor of 10 over the best coating method.

Obviously, it is preferable to have zero impurities in the medical device body. However, assuming that 0.075 milligrams of rhenium-185 have been added to a 17 milligram stent, the approximate weight percent of various contaminants in the stent alloy which produce 1 nanocurie of activity 14 days after neutron activation is given in the following list:

S=0.37%, Ca=0.59%, Sc=0.0002%, Cr=0.0039%, Fe=1.29%, Co=0.0042%, Zn=0.059%, Ge=0.0037%, Sr=0.85%, Y=0.010%, Zr=1.05%, Mo=0.37%, Ag=0.018%, Cd=0.21%, In=0.027%, Sn=0.39%, Sb=0.0029%, Ba=0.59%, Hf=0.0025%, Ta=0.0015%, W=0.037%, Bi=0.41%.

This list does not include reactive metals, rare earth elements, noble metals, halogens, and inert gases. The list additionally does not include the effect of branching ratio on gamma emitters. For example, while chromium is listed as 0.0039%, the value based on radiation emitted, rather than atoms decaying, is about 0.04 weight percent.

The amount of exposure required for neutron activation of the medical device depends on the flux rate of the nuclear reactor used, the thickness and composition of the coating applied to the body, and the amount of beta radiation desired. The exposure time could range from a few minutes in a very high flux reactor to several hours in a very low flux reactor. For example, for a coating that is approximately 700 Angstroms thick around the stent, an exposure time of roughly one-half hour in a high-flux reactor, such as, for example, the University of Missouri research reactor, which has a flux rate of about $8\times10^{14}$ neutrons per cm$^2$. This exposure for such a coating generally would yield approximately 4 microcuries of rhenium-186 beta radiation, and a negligible amount of contamination radiation from iron, chromium or cobalt contaminants in the medical device.

If the high-density coating is applied after the neutron activation of the medical device body, it may be fabricated in combination or individually of gold, platinum, iridium, or rhenium in addition to those elements that may be used for coating before neutron activation, i.e., rhodium, titanium, vanadium, manganese, copper, and praseodymium. The required properties are high-density, high atomic number, chemical inertness, and adhesion strength. If the thickness of the high-density coating is between five micrometers and twenty micrometers, it may also be utilized as a radiopaque material to improve x-ray visibility. When NiTi is employed, blocking of the nickel-63 beta particles requires a minimum thickness of approximately eight microns of gold. The advantage of applying the high-density coating after neutron activation is the freedom to select the highest density materials. The disadvantage is that personnel must handle a radioactive device during the coating procedure.

An alternate embodiment would be to apply a high-density coating prior to neutron activation of the medical device body. This alternate embodiment requires that the elements in the high-density coating must not activate to any radioisotopes with half-lives longer than either the 90.6 hours of rhenium-186 or the half-life of any other selected therapeutic radioisotope in the medical device body. The coating thickness must be sufficient to block the nickel-63 beta particles. In addition, if the high-density coating is also to be used for radiopacity, the coating requires sufficient density and thickness to exhibit good x-ray visibility. Examples of such elements, which may be employed in combination or individually, are rhodium, titanium, vanadium, manganese, copper, and praseodymium.

Rhodium or an alloy of rhodium-copper are preferred within this group. Rhodium has a density of 12.4, copper has a density of 9.0, and both are mutually miscible in all proportions. The copper is included to increase the ductility and reduce the stiffness of the rhodium. Neutron activation of stable rhodium-103 produces rhodium-104*, which has a 4.3 minute half-life. Neutron activation of stable copper-63 produces copper-64, which has a 12.7 hour half-life. Neutron activation of stable copper-65 produces copper-66, which has a 5.1 minute half-life. While rhodium has a lower density than gold or platinum, rhodium is more efficient at attenuating x-rays in the energy range between approximately 30 to 80 keV, which is in the central portion of a 120 keV tungsten bremsstrahlung x-ray spectrum commonly employed for medical imaging. As a consequence, rhodium and gold coatings of equal thickness are typically within five to ten percent of one another for x-ray radiopacity.

Figure 2:
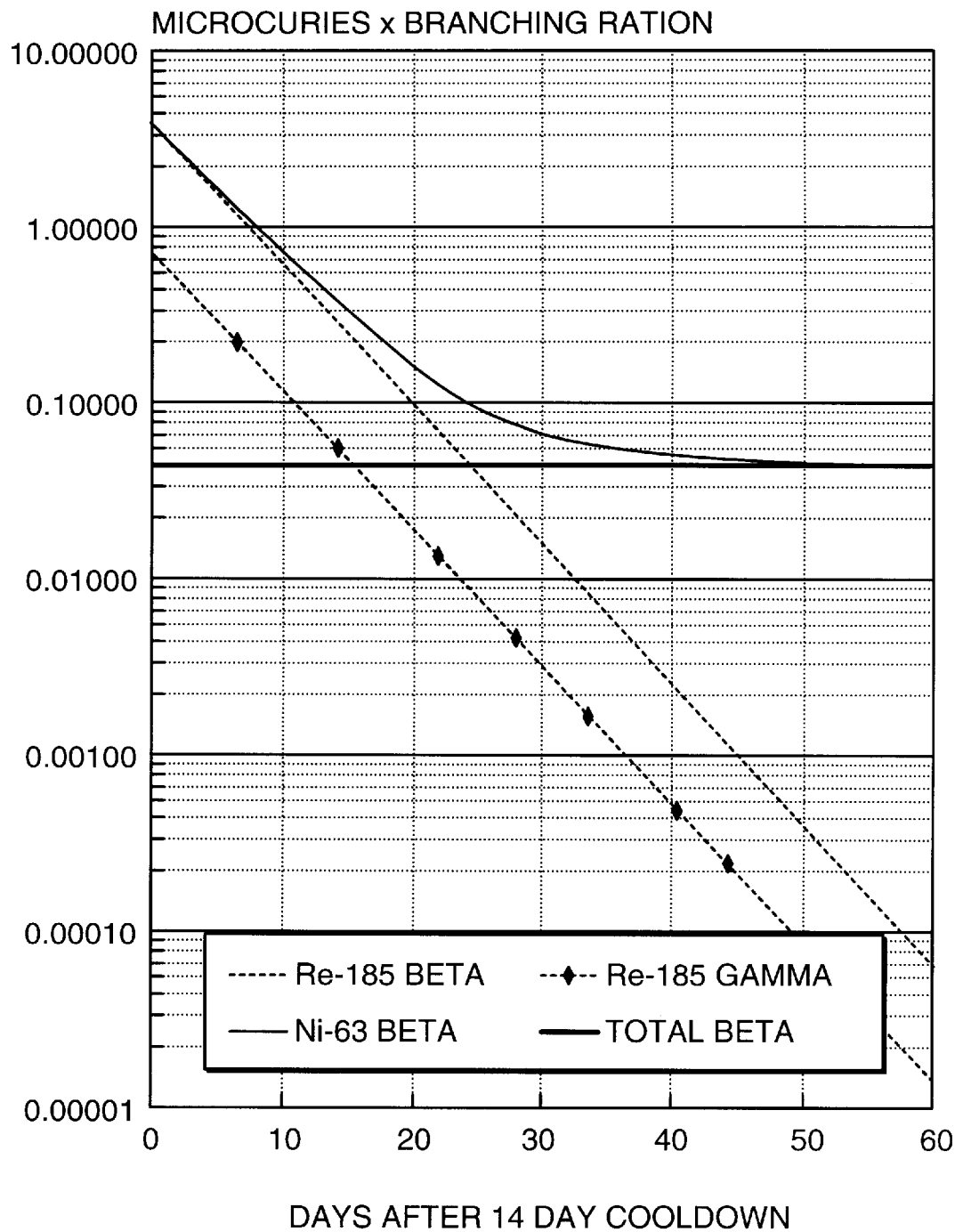
FIG. 2 shows the radioactive isotope decay history beginning at fourteen days after the removal from a reactor for a medical device fabricated from the titanium-nickel intermetallic compound known as nitinol that also includes an addition of seventeen micrograms of rhenium-185.

Nitinol primarily contains titanium and nickel. Titanium naturally exists as stable isotopes with masses between 46 and 50. Neutron activation of these stable titanium isotopes produces either stable isotopes or Ti-51, which has a short half-life of only 5.76 minutes. Such a short half-life implies that the radioactive Ti-51 will substantially decay to stable V-51 (vanadium-51) before any therapeutic use of the medical device and thus will be essentially non-existent. The nickel in nitinol can produce the radioisotopes Ni-59, Ni-63, Ni-65, and Ni-66. Ni-59 decays with no gamma or beta emission. Ni-65 has a short 2.517 hour half-life and can be ignored after fourteen days. Ni-66 is produced by a two step process which is highly inefficient, so little of the isotope is created. Ni-63 is produced relatively efficiently and has a 100 year half-life. FIG. 2 shows the calculated amount of each of these isotopes found in a stent fabricated from nitinol measured from a starting point fourteen days following removal from a nuclear reactor. Seventeen micrograms of Re-185 are also assumed to be in the stent. Ni-59, Ni-65, and Ni-66 have been eliminated from the figure because their activity is too small to be shown.

Ni-63 only decays with emission of a low energy beta particle of 66.9 keV end point energy. This beta particle has an energy which is low enough to be readily blocked by the thickness of a high-density coating, a thickness of about five micrometers of gold being required. Without the high-density coating, the activated Ni-63 would continuously emit beta particles into the artery wall for the life of the patient. Since this is not desirable, the high-density coating is useful if the medical device is fabricated from nitinol or any other material that contains a significant quantity of nickel.

The nitinol self-absorbs some of the emission of beta particles because of its own thickness. Assuming that the nitinol is in the form of a circular wire which is 0.0035 inches (0.0089 cm) in diameter, approximately 6.9% of the possible beta particle flux is still emitted. Nickel-62, the precursor of nickel-63, has a 3.59% natural abundance and a 14.5 barn cross section for neutron activation. Nickel-63 has a 24 barn cross section for conversion to stable nickel-64. Given a 17 mg nitinol stent, the nickel content is 11.3 mg and the nickel-62 content is 0.41 mg. Assuming a high flux reactor, such as the University of Missouri Reactor which has $8 \times 10^{13}$ neutrons/cm$^2$, after 1.25 hours of irradiation one obtains 0.122 microcuries of Ni-63. The actual apparent activity is 0.028 microcuries due to self absorption. This value of activity remains essentially constant for decades.

A gold coating of approximately ten to fifteen micrometers in thickness on the medical device body may enhance the x-ray image significantly. Gold is a very soft metal, and a thickness of ten to fifteen microns should not contribute additional structural stiffness to the body of the medical device. If the medical device body is a stent, it should have considerable stiffness in order to hold open the elastic artery.

In order to effect good adhesion of the gold coating to the medical device body, it is desirable to first coat the structure with a thin coating of titanium about 3000 Angstroms thick before depositing the thicker gold coating. Titanium has been found to promote adhesion to nitinol stents. Both the adhesion promoting layer and the gold coating can be deposited using an unbalanced magnetron sputtering process in vacuum.

While the invention has been disclosed in connection with the preferred embodiments shown and described in detail, various modifications and improvements will be apparent to one of ordinary skill in the art from the above description.

We claim:

1. An implantable device comprising:
   a body comprising a nickel-containing metal alloy or a combination of metals which includes nickel;
   a non-radioactive precursor isotope disposed within or about said body; and
   a high-density metal coating disposed over at least a portion of said body containing said non-radioactive precursor isotope.

2. The implantable device of claim 1, wherein the body comprises at least about 8% by weight of nickel.

3. The implantable device of claim 1, wherein said body is substantially free of iron and chromium.

4. The implantable device of claim 1, wherein said alloy comprises nitinol.

5. The implantable device of claim 1, wherein said non-radioactive precursor comprises $^{185}$Re or $^{187}$Re.

6. The implantable device of claim 1, wherein said high density coating comprises a metal selected from the group consisting of palladium, platinum, iridium, praseodymium, rhodium, rhenium and gold.

7. The implantable device of claim 1, wherein said high density coating has a thickness sufficient to block beta particle emissions of nickel-63 from the device.

8. The implantable device of claim 7, wherein said high density coating is between approximately 5 micrometers and approximately 20 micrometers thick.

9. The implantable device of claim 1, further comprising an adhesion coating disposed between said body and said non-radioactive precursor isotope.

10. The implantable device of claim 9, wherein said adhesion coating comprises a material selected from the group consisting of: aluminum, silicon, titanium, vanadium, manganese, copper, nickel, rhodium and combinations thereof.

11. The implantable device of claim 1, wherein said high density metal coating comprises the same metal as the non-radioactive precursor isotope.

12. The implantable device of claim 11, wherein said metal is rhenium.

13. A radioactive implant made by exposing to thermal neutrons a non-radioactive device comprising:
   a body comprising a nickel-containing metal alloy or a combination of metals which includes nickel;
   a non-radioactive precursor isotope disposed within or about said body; and
   a high-density metal coating disposed over at least a portion of said body containing said non-radioactive precursor isotope;

said exposure to thermal neutrons being sufficient to transform at least a portion of the non-radioactive precursor isotope to a radioactive isotope.

14. The radioactive implant of claim 13, wherein said thermal neutron exposure exceeds a dose of about $8 \times 10^{13}$ neutrons/cm$^2$.

15. The radioactive implant of claim 13, wherein said high density coating has a thickness sufficient to block beta particle emissions of nickel-63 from the device.

* * * * *